(12) United States Patent
Koyama (10) Patent No.: US 10,401,004 B2
(45) Date of Patent: Sep. 3, 2019

(54) HEAD-MOUNTED TYPE LIGHTING DEVICE

(71) Applicant: TAIYO CORPORATION, Tokyo (JP)

(72) Inventor: Mitsuhiro Koyama, Tokyo (JP)

(73) Assignee: TAIYO CORPORATION, Tokyo (JP)

( * ) Notice: Subject to any disclaimer, the term of this patent is extended or adjusted under 35 U.S.C. 154(b) by 124 days.

(21) Appl. No.: 15/797,584

(22) Filed: Oct. 30, 2017

(65) Prior Publication Data

US 2018/0306418 A1      Oct. 25, 2018

Related U.S. Application Data (63) Continuation of application No. PCT/JP2017/015680, filed on Apr. 19, 2017.

(51) Int. Cl.

| F21V 21/084 | (2006.01) |
| F21K 9/60 | (2016.01) |
| F21V 13/04 | (2006.01) |
| F21V 21/14 | (2006.01) |
| A61B 90/30 | (2016.01) |
| A61B 90/35 | (2016.01) |

(Continued)

(52) U.S. Cl.
CPC .......... *F21V 21/084* (2013.01); *A61B 90/30* (2016.02); *A61B 90/35* (2016.02); *F21K 9/60* (2016.08); *F21V 13/04* (2013.01); *F21V 21/145* (2013.01); *A61B 2090/309* (2016.02); *A61B 2090/502* (2016.02); *F21Y 2115/10* (2016.08)

(58) Field of Classification Search
CPC . F21V 21/084; A61B 90/30; A61B 2090/502; A61B 1/06

USPC ......................................................... 362/105
See application file for complete search history.

(56) References Cited

U.S. PATENT DOCUMENTS

| 4,104,709 A | * | 8/1978 | Kloots | .................... F21L 14/00 |
| | | | | 362/105 |
| 5,774,271 A | * | 6/1998 | Lagerway | ............... F21L 14/00 |
| | | | | 359/649 |

(Continued)

FOREIGN PATENT DOCUMENTS

| JP | 2014-500594 A | 1/2014 |
| JP | 2014-135277 A | 7/2014 |

(Continued)

OTHER PUBLICATIONS

PCT/ISA/210, "International Search Report for International Application No. PCT/JP2017/015680," dated Jul. 25, 2017.

*Primary Examiner* — William N Harris
(74) *Attorney, Agent, or Firm* — Manabu Kanesaka (57) ABSTRACT

A lighting device includes a main body including a belt-shaped portion mounted along a circumferential direction of a head of a wearer, a storage case provided in the main body and positioned in a forehead region of the wearer when the lighting device is mounted on the wearer, and a light source unit that is incorporated in the storage case and includes a light emitting diode (LED) substrate on which a plurality of LED light sources is mounted. The light source unit includes a condensing lens for condensing light emitted from the plurality of LED light sources, a reflecting mirror for deflecting light emitted from the condensing lens and reflecting the light toward an affected part of a patient, and a radiator plate that radiates heat generated from the LED substrate and extends from a forehead region toward a parietal region of the wearer.

12 Claims, 10 Drawing Sheets

(51) Int. Cl.
*A61B 90/50* (2016.01)
*F21Y 115/10* (2016.01)

(56) References Cited

U.S. PATENT DOCUMENTS

| | | | | |
|---|---|---|---|---|
| 2008/0316733 | A1* | 12/2008 | Spartano | F21L 14/00 362/105 |
| 2011/0160541 | A1 | 6/2011 | Koyama et al. | |
| 2012/0120635 | A1 | 5/2012 | Strong et al. | |
| 2014/0198484 | A1 | 7/2014 | Feustel et al. | |
| 2014/0334132 | A1* | 11/2014 | Ferguson | A61B 90/35 362/105 |
| 2014/0336472 | A1* | 11/2014 | Ferguson | A61B 90/35 600/249 |
| 2016/0207228 | A1* | 7/2016 | Ferguson | B29C 39/10 |

FOREIGN PATENT DOCUMENTS

| | | | |
|---|---|---|---|
| JP | 5642545 | B2 | 11/2014 |
| JP | 2015-019886 | A | 2/2015 |

* cited by examiner

HEAD-MOUNTED TYPE LIGHTING DEVICE

CROSS-REFERENCE TO RELATED APPLICATION

This is a continuation application of PCT International Application No. PCT/JP2017/015680 filed on Apr. 19, 2017, the disclosure of which is incorporated herein.

TECHNICAL FIELD

The present invention relates to a lighting device that irradiates an affected part when a medical staff such as a doctor gives various treatments to a patient, and in particular, relates to a lighting device attachable to a head.

BACKGROUND ART

Conventionally, a medical institution such as a hospital is equipped with an operating room and a treatment room, and a surgical light for irradiating an affected part at the time of performing a treatment on a patient is installed in these rooms. The surgical light has a structure that irradiates the affected part with high illuminance light, and a halogen lamp, etc. has been used as a light source. Besides, recently, a light emitting diode (LED) light source using an LED has been used as the light source. In this case, according to the IEC standard (IEC 60601-2-41) on illuminators for medical use, regarding a light field diameter and illuminance, it is necessary that a maximum illuminance value is 40000 LUX or more, and an illuminance value of 50% or more of the maximum illuminance value is ensured within a range of 50% from a center of an effective light field diameter (marked in a catalog, etc. of a product).

However, the above-described indoor installation type surgical light is high priced, and such surgical light equipment may not be installed depending on the medical institution. In addition, in the event of emergency such as disaster, conflict, etc., when emergency action is taken on a patient, the patient may not be urgently transported to a medical institution having the surgical light equipment or a treatment room in which the surgical light equipment is installed.

Therefore, in order to solve such a problem, Patent Document 1 discloses a head-mounted type lighting device which can be worn on a head of a medical staff to irradiate the affected part. The lighting device disclosed in Patent Document 1 incorporates a light-emitting unit that can ensure illuminance equivalent to that of the surgical light installed in the operating room, etc. and can be utilized in an emergency, etc.

Specifically, the head-mounted type lighting device disclosed in Patent Document 1 (hereinafter also referred to as a lighting device) includes a headband attached over a whole circumference of the head of the medical staff and a support band fixed to the headband and arranged to cross a top region of the head of the medical staff. These bands are adjustable in a lengthwise direction and configured to be attachable to different sizes of heads. A light-emitting unit incorporating a mounting board on which a large number of LEDs (LED light sources) are mounted is attached to a forehead region of the headband, and a support member through which the headband is inserted is provided in the light-emitting unit. In this case, the light-emitting unit is supported to be rotatable in a vertical direction through a spindle with respect to the support member, and an irradiation angle of light emitted from the LED light source may be adjusted when the light-emitting unit is gripped and rotated in the vertical direction. In addition, the LED light source incorporated in the light-emitting unit is configured such that illuminance of an irradiated part is 30,000 to 60,000 LUX even when the LED light source is 600 mm away from a front surface of the light-emitting unit. Further, even when the LED light source is used in the head-mounted type lighting device, irradiation light having high illumination may be obtained.

CITATION LIST

Patent Document
  Patent Document 1: JP 5642545 B2 (WO 2010/007785 A1)

SUMMARY OF THE INVENTION

Problem to be Solved by the Invention

According to the lighting device as described above, the medical staff may apply appropriate measures to the patient even when large-scale surgical light equipment is not provided. In addition, such a lighting device may be used in combination in an operating room, etc. in which normal surgical light equipment is installed.

Incidentally, when the medical staff performs a treatment on the patient, it may take a long time. Various problems below arise in terms of practicality in a known lighting device equipped with a light-emitting unit in which a high-illumination LED light source is incorporated in a headband.

When the medical staff (hereinafter also referred to as a wearer) wears the lighting device for a long time, the weight acting on the head is burdensome. In particular, the weight acting on the head is a burden in carrying out detailed treatment actions, and it is preferable that the weight of the entire device is reduced as much as possible. In addition, it is preferable that the weight acting on the wearer is on a parietal region side (on an extension of a bone of a neck) as much as possible. When the weight concentrates on a position away from the parietal region, fatigue feeling and discomfort increase with wearing for a long time. The above-described known lighting device has a structure in which the light-emitting unit corresponding to a heavy object is rotatably supported by the support member through the spindle in front of the forehead of the wearer, and has a weight balance in which a weight body locally concentrates in front of the forehead of the wearer. For this reason, when the lighting device is worn for a long time, a weight burden felt by the wearer is large, and operability and a handling property are poor.

In addition, since the LED light source for obtaining high illuminance is incorporated in the light-emitting unit, heat generation is a serious problem. Unless a heat radiation process is appropriately performed, the equipment may be broken or the wearer may not continue to wear the device for a long time. In the known lighting device described above, heat radiation is performed by incorporating a cooling fan in the light-emitting unit or incorporating a thermoelectric element such as a Peltier element. However, there are the following problems.

Incorporating the cooling fan in the light-emitting unit causes air convection, and thus, for example, the cooling fan may not be used in a sterile operating room. In addition, since the thermoelectric element such as the Peltier element consumes a large amount of power, battery consumption is intense, and thus a light emission time of the LED is shortened. Therefore, the lighting device used as a portable device may not ensure a sufficient irradiation time.

In addition, incorporating such a cooling fan or a Peltier element in the light-emitting unit increases the weight of the light-emitting unit, so that a heavy object concentrates in front of the forehead, and the above-mentioned weight balance problem becomes conspicuous.

In addition, changing an irradiation range of the irradiation light from the LED light source in the vertical direction requires the light-emitting unit corresponding to a weight body to be rotated in the vertical direction with respect to the support member, and operability is poor. Furthermore, changing the light field diameter (depth adjustment) is not sufficiently considered, which is inferior in terms of the handling property.

An object of the present invention to provide a head-mounted type lighting device which has an excellent weight balance, may exhibit a sufficient heat radiation effect even when a high-illuminance light-emitting unit is included, and is excellent in a handling property and operability.

Means for Solving Problem

To achieve the above-mentioned object, a head-mounted type lighting device according to the invention includes a main body including a belt-shaped portion mounted along a circumferential direction of a head of a wearer, a storage case provided in the main body and positioned in a forehead region of the wearer when the lighting device is mounted on the wearer, and a light source unit incorporated in the storage case, the light source unit including a light emitting diode (LED) substrate, a plurality of LED light sources being mounted on the LED substrate, in which the light source unit includes a condensing lens for condensing light emitted from the plurality of LED light sources, a reflecting mirror for deflecting light emitted from the condensing lens and reflecting the light toward an affected part of a patient, and a radiator plate for radiating heat generated from the LED substrate, the radiator plate extending from a forehead region toward a parietal region of the wearer.

Effect of the Invention

The invention obtains a head-mounted type lighting device which has an excellent weight balance, may exhibit a sufficient heat radiation effect even when a high-illuminance light-emitting unit is included, and is excellent in a handling property and operability.

MODE(S) FOR CARRYING OUT THE INVENTION

Hereinafter, a description will be given of an embodiment of a head-mounted type lighting device according to the invention with reference to accompanying drawings.

First, an overall configuration of the lighting device will be described with reference to FIG. 1 to FIG. 5.

The lighting device 1 has a main body 3 including a belt-shaped portion 3a attached along a circumferential direction of a head H of a medical staff (also referred to as a wearer) P. The main body 3 is preferably made of a lightweight flexible material, for example, integrally formed of a synthetic resin such as polypropylene. The belt-shaped portion 3a is mounted along a circumference of the head at an upper side of both ears E of the head H, protrusions 3b protruding forward from the forehead at the time of being mounted on the head H are formed on a front side of the belt-shaped portion 3a on both sides, and a light source unit 20 to be described below is arranged in this portion.

It is preferable that a shade portion 3c is integrally formed on the main body 3 above the protrusion 3b to protrude forward from a forehead portion of the wearer P. When such a shade portion 3c is integrally formed, it is possible to block external light other than light irradiated from the light source unit 20 (for example, light from an installation-type surgical light when it is used in combination with the lighting device 1) from an eye of the wearer P at the time of treating a patient, and it is possible to concentrate on a medical treatment.

A length adjusting mechanism 40 to be described below is arranged in a part of the belt-shaped portion 3a to be fittable to various sizes of heads of wearers. The length adjusting mechanism 40 of the present embodiment is arranged by dividing the belt-shaped portion 3a at a rear of the head H, and a length of the belt-shaped portion 3a may be adjusted by rotating an adjusting knob 47.

The main body 3 is provided with a holding member that stably holds the lighting device by coming into contact with a surface of the head at the time of being worn by the wearer. This holding member includes a curved front cushion member 61 with which the head surface comes into contact from an upper part of the forehead of the wearer toward the parietal region when the main body 3 is attached to the head H, and a curved back cushion member 62 with which the head surface comes into contact from a parietal area of the wearer toward an occipital region side. As described above, since the main body 3 is regulated by the belt-shaped portion 3a whose length in a left-right direction of the head is adjusted, and a front-rear direction and a vertical direction of the head are regulated by the curved cushion members 61 and 62 coming into contact with narrow regions of the head surface, it is possible to expose a large part of the head surface (a part other than the cushion members 61 and 62). In this way, it is possible to stably attach the lighting device to the head while reducing the weight of the main body as much as possible.

It is preferable that the front cushion member 61 and the back cushion member 62 are made of foamable urethane, etc. so that their weights are reduced and contact with the head is excellent. In addition, it is preferable that these cushion members are attached to a front hub 61*a* and a back hub 62*a* made of polypropylene, etc. such that a holding state with respect to the main body 3 is stabilized, and these members are attached to the main body 3 through a stopper screw 65 (only the front hub 61 side is illustrated).

The light source unit 20 is attached to a position corresponding to the forehead region in the main body 3 at the time of being mounted on the head. The light source unit 20 includes an LED substrate on which a plurality of LED light sources is mounted, and the LED light sources of the present embodiment have a specification that ensures brightness suitable for a medical treatment. Specifically, as described below, a used LED light source may ensure brightness of about 65,000 LUX with respect to an affected part of a patient, which is about 400 mm to 500 mm away from eyes of the wearer. Therefore, since the LED substrate serves as a large heat source, heat radiation means needs to be provided to efficiently radiate heat therefrom. The heat radiation means in the invention includes a substantially rectangular radiator plate 70 extending from the light source unit (the forehead region of the wearer) toward a parietal region of the wearer, and the radiator plate 70 is formed in a plate shape using a material (a material having excellent heat conductivity) that efficiently conducts heat by being thermally connected to the LED substrate, for example, aluminum, iron, copper, etc.

Figure 1:
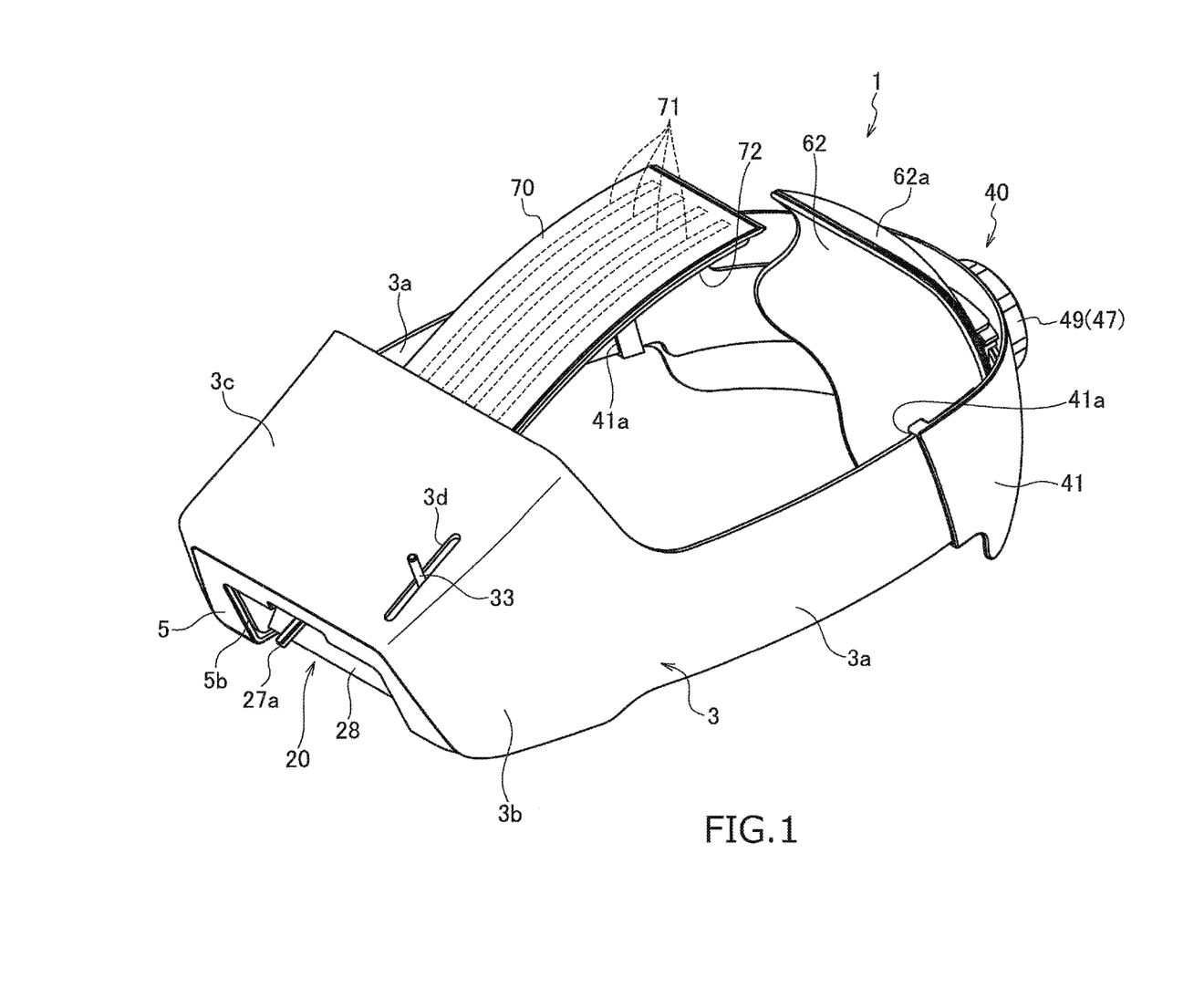
FIG. 1 is a diagram illustrating an embodiment of a head-mounted type lighting device according to the invention, and is a perspective view viewed from a front side.
Figure 2:
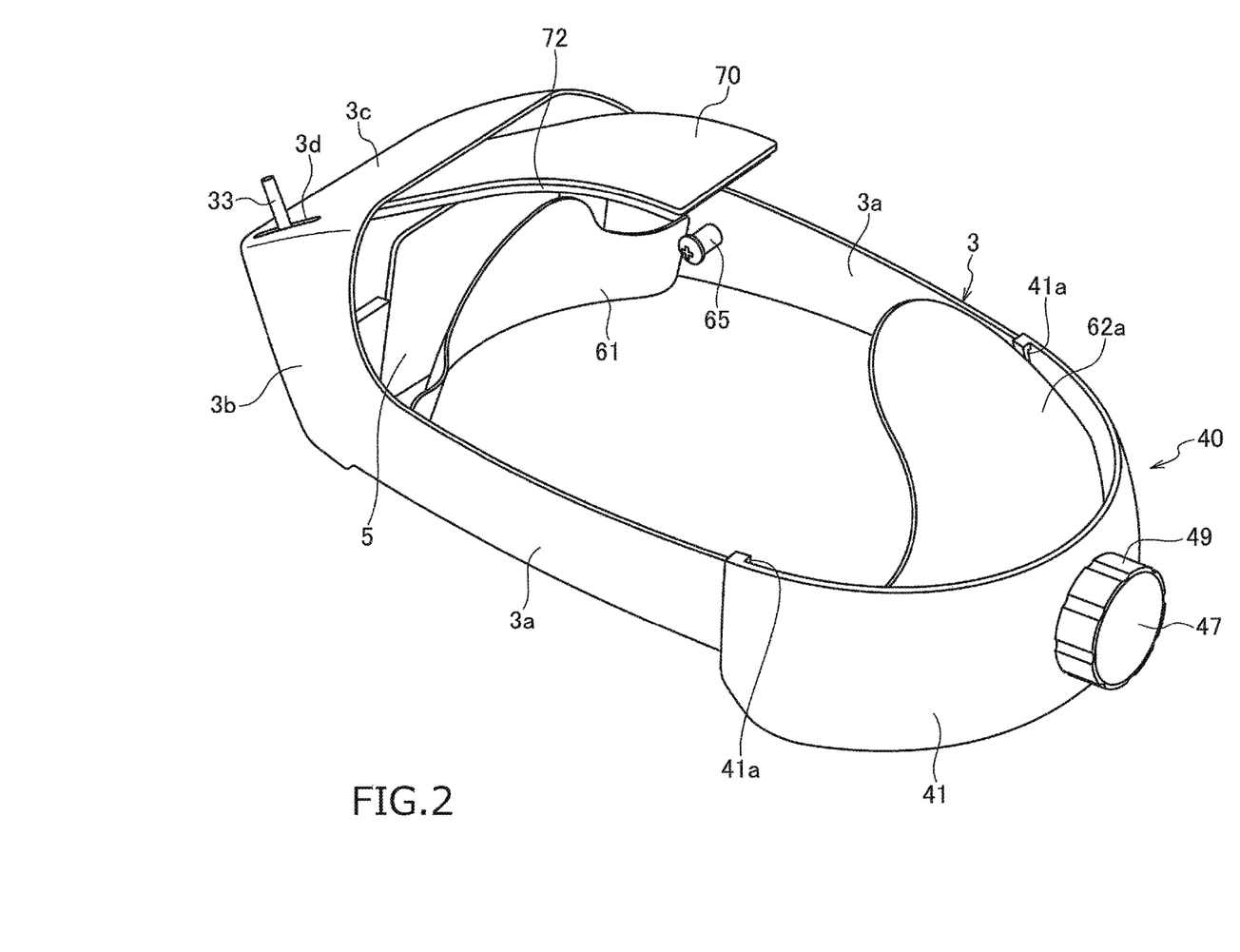
FIG. 2 is a perspective view of the lighting device illustrated in FIG. 1 viewed from a rear side.
Figure 3:
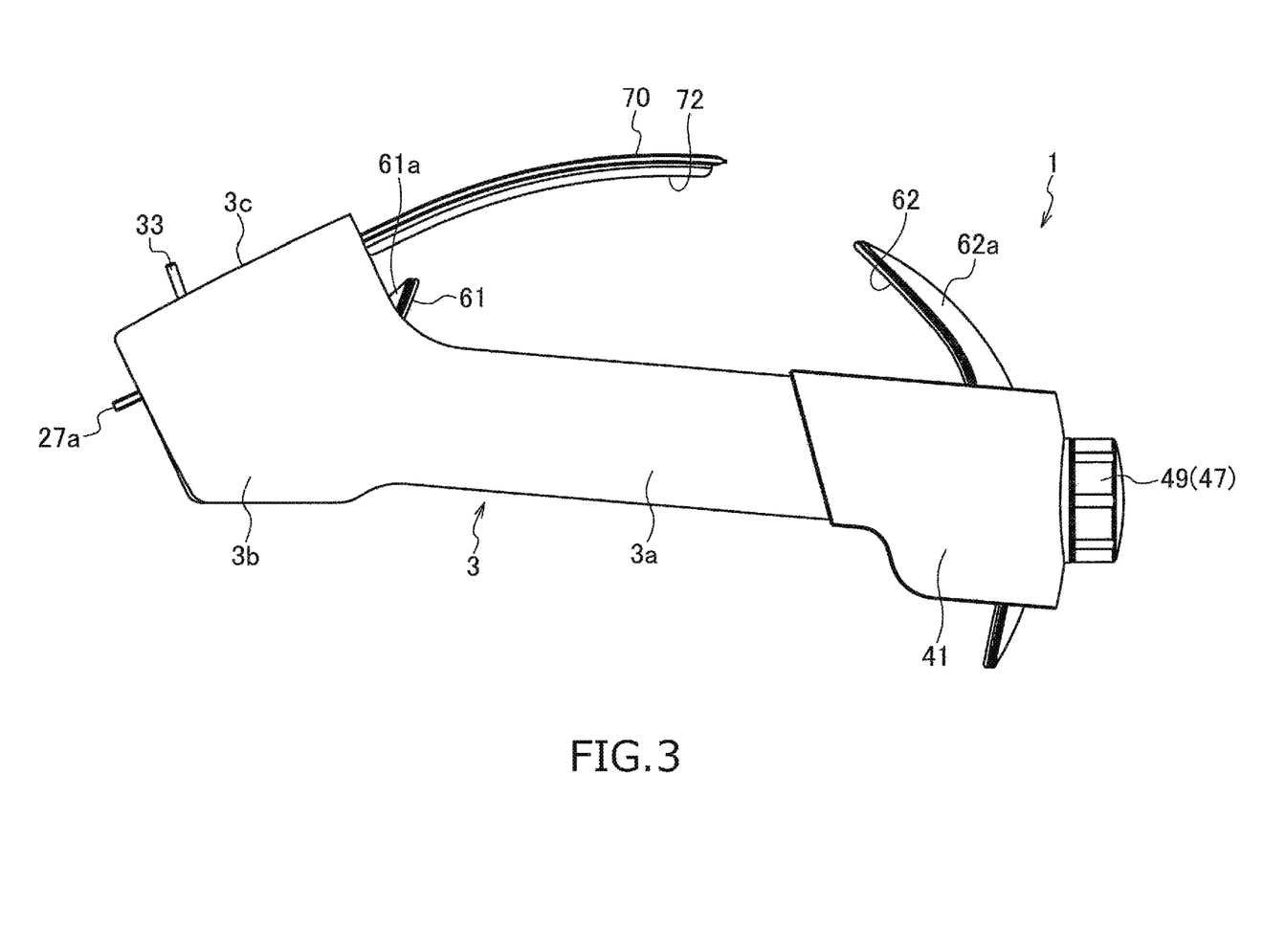
FIG. 3 is a side view of the lighting device illustrated in FIG. 1.
Figure 4:
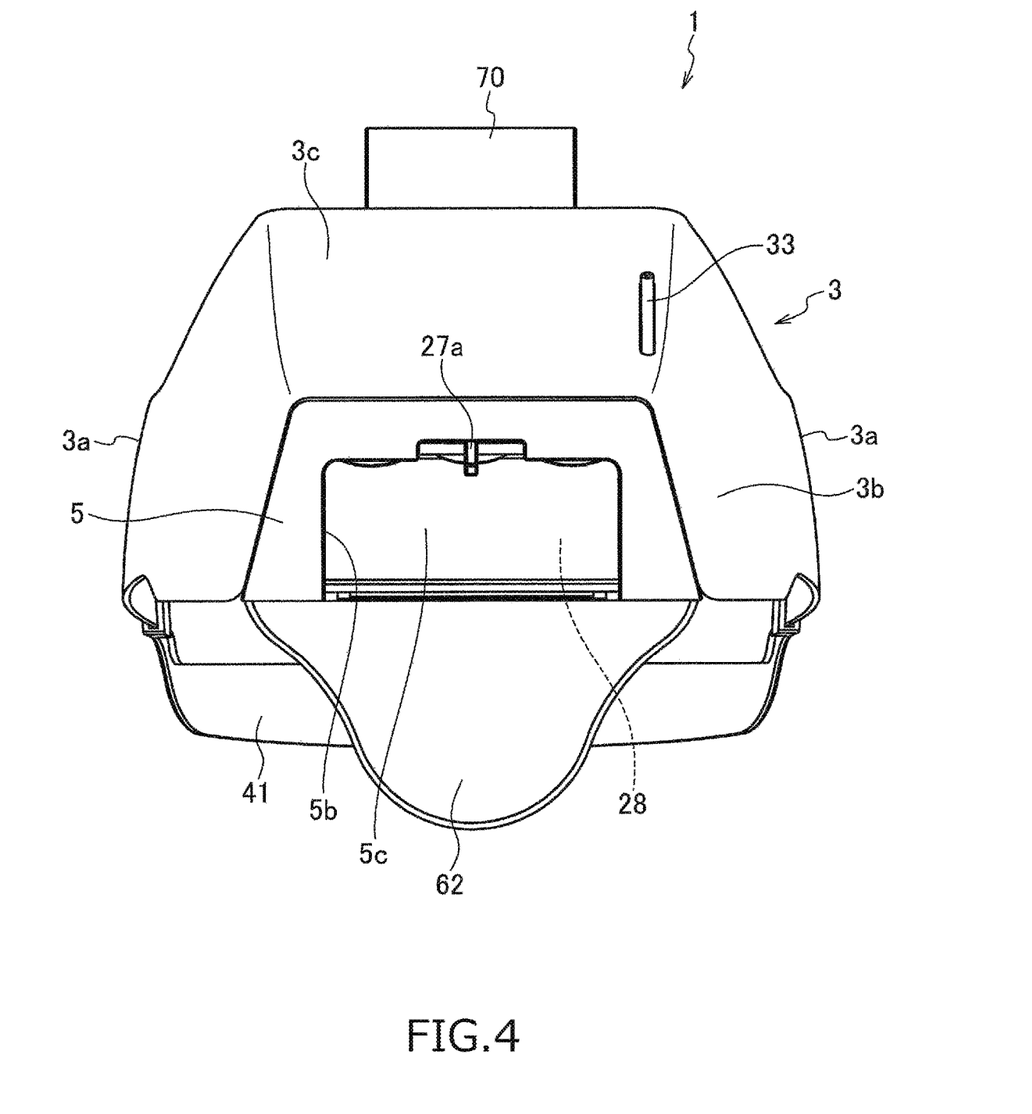
FIG. 4 is a front view of the lighting device illustrated in FIG. 1.
Figure 5:
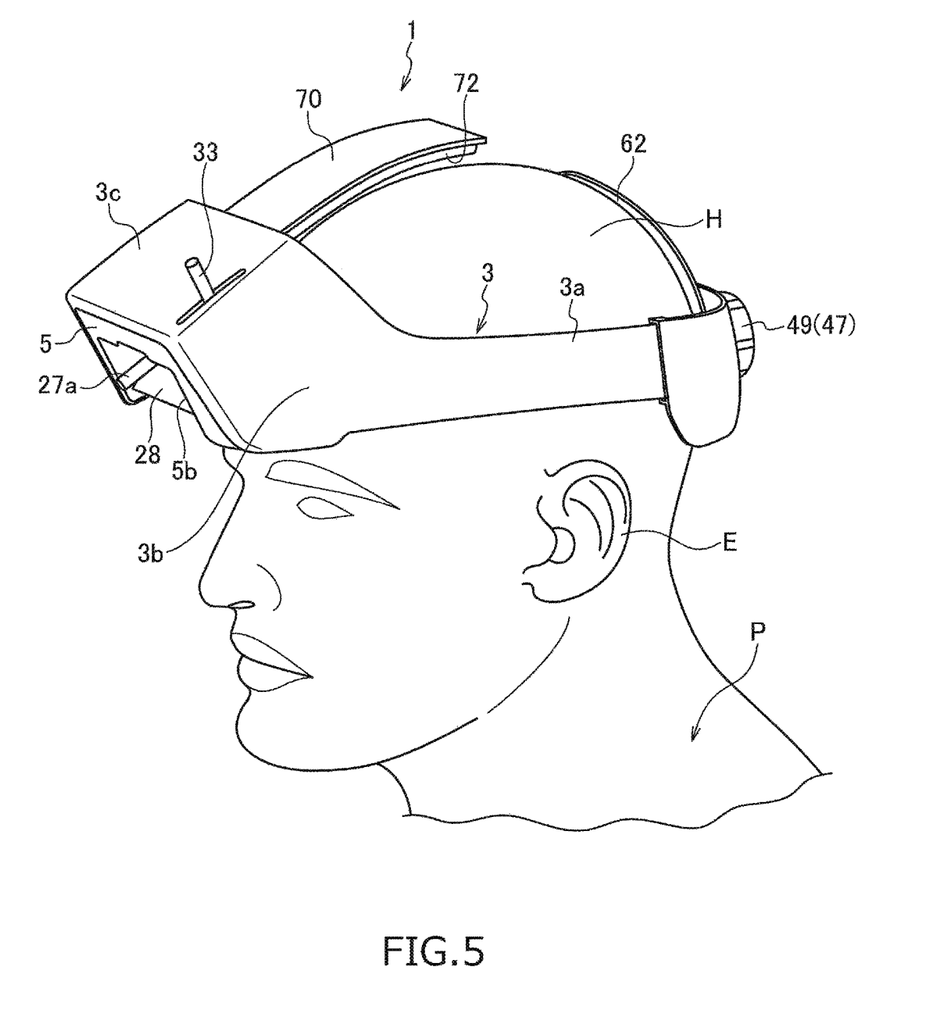
FIG. 5 is a perspective view illustrating a state in which the lighting device is mounted on a head.

The radiator plate 70 may be arranged to extend upward from the forehead with respect to the main body 3 to easily radiate heat upward. However, as illustrated in FIG. 5, it is preferable that the radiator plate 70 is formed in a curved shape such that a substantially uniform distance is maintained with respect to the surface of the head H of the wearer, and has a shape that terminates at a top region of the wearer. When the shape of the radiator plate is formed such that the distance to the head surface is substantially uniform in a whole region as described above, the wearer feels substantially uniform radiant heat from the radiator plate, and a feeling of discomfort does not occur during use. That is, in a case in which the radiator plate is arranged on the head, when the distance to the surface of the head H is different, a portion close to the surface is hot, and less heat is felt at a portion far from the surface. Therefore, a temperature difference is felt in a region of the radiator plate, which causes the feeling of discomfort during use. When the plate-shaped radiator plate is formed in a shape that maintains a substantially uniform distance from the surface of the head as illustrated in FIG. 5, the temperature difference is not felt during use.

The radiator plate 70 may have a configuration to incline upward in a straight line shape from the forehead to an upper side. However, in such a configuration, the radiator plate is in a rising state, obstructive in terms of image, and inferior in design. When an arrangement mode illustrated in FIG. 5 is adopted at the time of wearing, a simple-looking design is obtained, and the radiator plate is not obstructive during handling, etc. In addition, a terminal position of the radiator plate 70 preferably terminates in the top region of the wearer. In a use state in which the patient is being treated, the wearer somewhat faces downward. When the terminal position of the radiator plate terminates in the top region, the terminal position terminates at a highest position, and thus efficiency of heat radiation is most excellent.

A material and shape of the radiator plate 70 are not particularly limited. However, it is preferable that not only heat is radiated from the surface but also a heat pipe 71 extending in a longer direction is incorporated in the inside thereof (see FIG. 1). Such a heat pipe 71 is filled with a hydraulic fluid. When heat in the substrate is transferred to the hydraulic fluid, the hydraulic fluid is vaporized, rises to an upper part, cooled in this part, returns to a liquid, and returns to a heat source area due to gravity thereof. Thus, when the shape and the arrangement mode of the radiator plate 70 are configured as described above, and the heat pipe 71 is incorporated therein, heat may be efficiently radiated.

The above-described radiator plate 70 is preferably covered with a heat insulating member (for example, a foamable silicone member for heat shielding) 72 on a surface on the head side. When the radiator plate 70 is covered with the heat insulating member 72, heat radiated from the radiator plate is hardly felt, and a feeling of discomfort (a feeling of discomfort due to feeling of heat) does not occur after wearing for a long time. In addition, when the radiator plate 70 is formed in the curved shape along the surface of the head as described above, it is preferable that an average surface shape of the head is calculated according to an area (country) in which the device is used, and a curved shape is formed to be suitable for a head shape of a person in the area.

According to the heat radiation means described above, an air cooling fan, a Peltier element, etc. may not be incorporated in the light source unit, a light source unit part may be reduced in weight, and a position of a center of gravity of the entire main body 3 to be mounted may be shifted to a center side of the head by the radiator plate 70 extending backward. Therefore, since concentration of the weight in front of the forehead is relieve, a weight bearing feeling on the wearer may be alleviated, and fatigue, etc. less likely to occur after wearing for a long time.

Next, a description will be given of configurations of the light source unit 20 and the length adjusting mechanism 40 arranged in the main body 3 with reference to FIG. 6 to FIG. 9.

The light source unit 20 is incorporated in a storage case 5 mounted to be located in the forehead region of the wearer when the main body 3 is mounted on the wearer. The storage case 5 is formed by molding a lightweight material excellent in rigidity, hardness, workability, etc., for example, ABS resin into a substantially V shape, and the light source unit 20 is installed inside the storage case 5 and positioned and fixed by a screw 5*a*, etc. Further, the storage case 5 in this state is connected to a forehead side region of the main body 3. In the present embodiment, the storage case 5 is connected to a lower side of the shade portion 3*c* between the protrusions 3*b* on both sides of the main body 3. Further, the storage case 5 and the main body 3 may be connected by a locking structure using elastic deformation or may be connected by a simple connecting member, for example, a screw which may be manually rotated by hand, etc. so that the storage case is not easily separated. In addition, a substantially rectangular opening 5*b* is formed at a front side of the storage case 5, and light from the light source unit 20 is emitted through this opening. It is preferable to attach a transparent protective plate 5*c* to the opening 5*b* to protect an optical element (a reflecting mirror, etc.) of the light source unit 20.

The light source unit 20 includes a base 21 having side walls 21*a* parallel to each other and an upper wall 21*b* that connects the side walls. Further, an LED substrate 24 on which an LED element serving as a light source is mounted, various optical elements for irradiating a predetermined position (affected part of the patient) with LED light emitted from the LED light source, and the radiator plate 70 are installed between the side walls 21a.

A substrate base 22 is attached to a rear surface of the upper wall 21b by a screw 22a from a surface side in a state in which a proximal end side of the radiator plate 70 is interposed therebetween. The LED substrate 24 on which a plurality of LED elements (not illustrated) is mounted is attached to the substrate base 22 by a screw 22b. The LED elements are mounted on a lower surface, and LED light is irradiated downward.

Light emitted from each of the LED elements is condensed by a condensing lens. The condensing lens functions to condense a large number of LED light rays and illuminate the affected part of the patient, and light may be condensed by one condensing lens. However, considering a specialty of condensing light at a position of a certain distance in a certain light field diameter range at high illuminance as in the invention, it is desirable to arrange a plurality of condensing lenses (in the present embodiment, irradiation light is condensed at a certain light field diameter using three condensing lenses).

The above-mentioned certain distance refers to an approximate distance from a position equivalent to the eyes of the wearer to the affected part (indicated by L in a schematic view of FIG. 9), and is about 400 to 500 mm in the present embodiment. In addition, the above-mentioned certain light field diameter refers to a range in which the affected part is irradiated (an effective light field diameter displayed in a catalog, etc., indicated within a range of R2 in the schematic view of FIG. 9), and the diameter is set to about 150 mm the present embodiment. In addition, in the present embodiment, the above-mentioned high illumination means that illumination of 65,000 LUX is ensured at a center position of a certain light field diameter (indicated by C in the schematic view of FIG. 9), illumination of 32,500 LUX is ensured at a position of a diameter 90 mm from the center position (indicated by R1 in the schematic view of FIG. 9), and illumination of 6,500 LUX is ensured at a position of a diameter 150 mm from the center position (indicated by R2 in the schematic view of FIG. 9). This illumination satisfies the above-mentioned IEC standard (IEC 60601-2-41; see FIG. 10).

The three condensing lenses have the same configuration and are installed inside three lens barrels 25a, 25b, and 25c attached to the LED element side of the LED substrate 24 by a screw 22c. In this case, it is preferable to provide a helicoid mechanism in the lens barrels 25a, 25b, and 25c so that each condensing lens may be integrally shifted in an optical axis direction. As is generally known, the helicoid mechanism has a function of shifting the condensing lenses held in each of the lens barrels 25a, 25b, and 25c in the optical axis direction. In the present embodiment, the helicoid mechanism is configured to integrally rotate the respective lens barrels and integrally shift the respective condensing lenses in an axial direction by integrally driving respective projecting pieces 26 projecting forward in the left-right direction.

Specifically, a connecting member 27 extending in a lateral direction is connected to each of the projecting pieces 26 projecting forward by a screw 22d, and a lens barrel rotation operation member (operation lever) 27a is formed on the connecting member 27 to protrude forward from the main body 3. Further, when the operation lever 27a protruding forward from the main body 3 (a part of the shade portion 3c) is pinched and operated to slide in the left-right direction, it is possible to integrally rotationally drive the respective lens barrels 25a, 25b, and 25c, and to integrally shift the condensing lenses held therein in the axial direction.

Here, a description will be given of an effect of the condensing lens held in each of the lens barrels with reference to the schematic view of FIG. 9.

Figure 9:
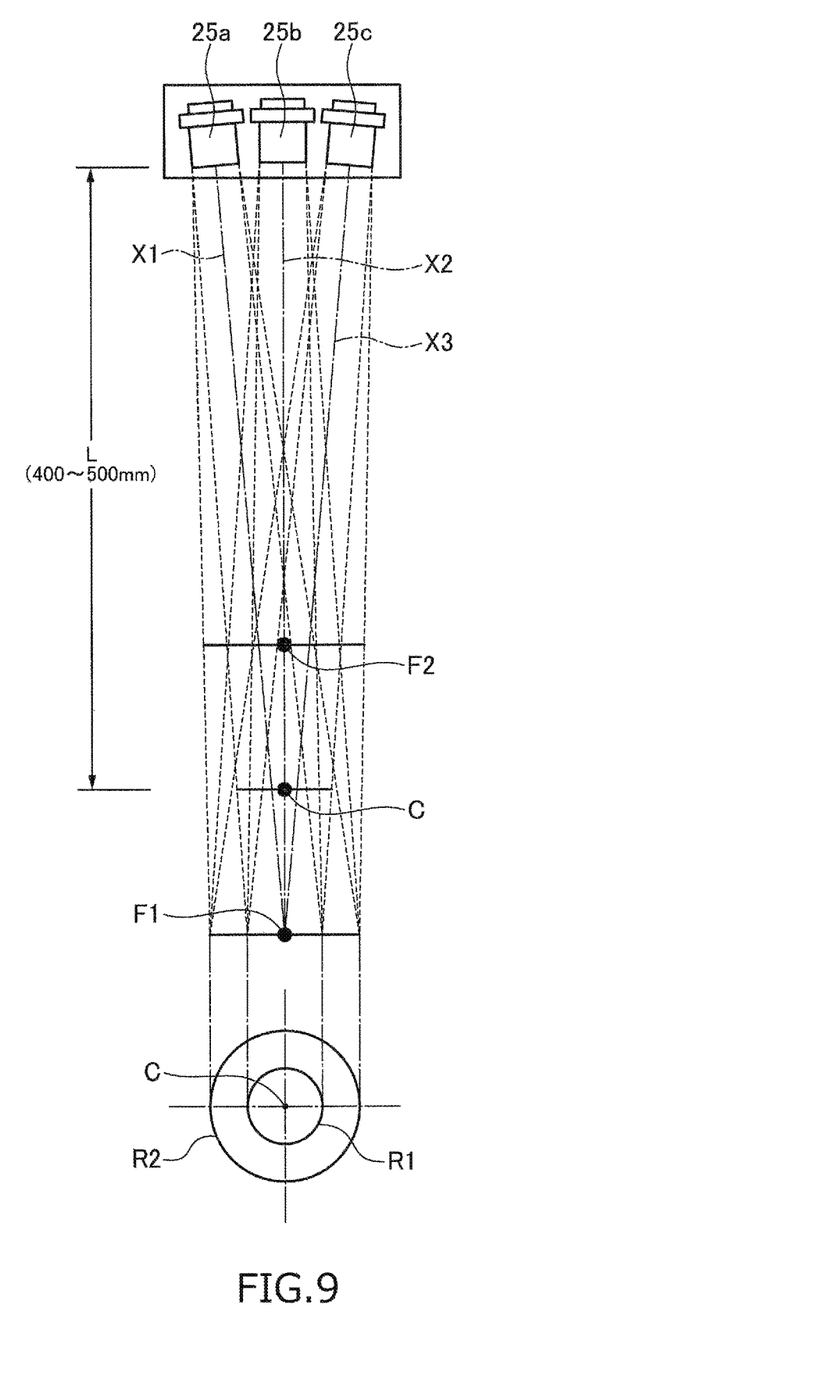
FIG. 9 is a schematic view of paths of lights by condensing lenses incorporated in the light source unit.
Figure 10:
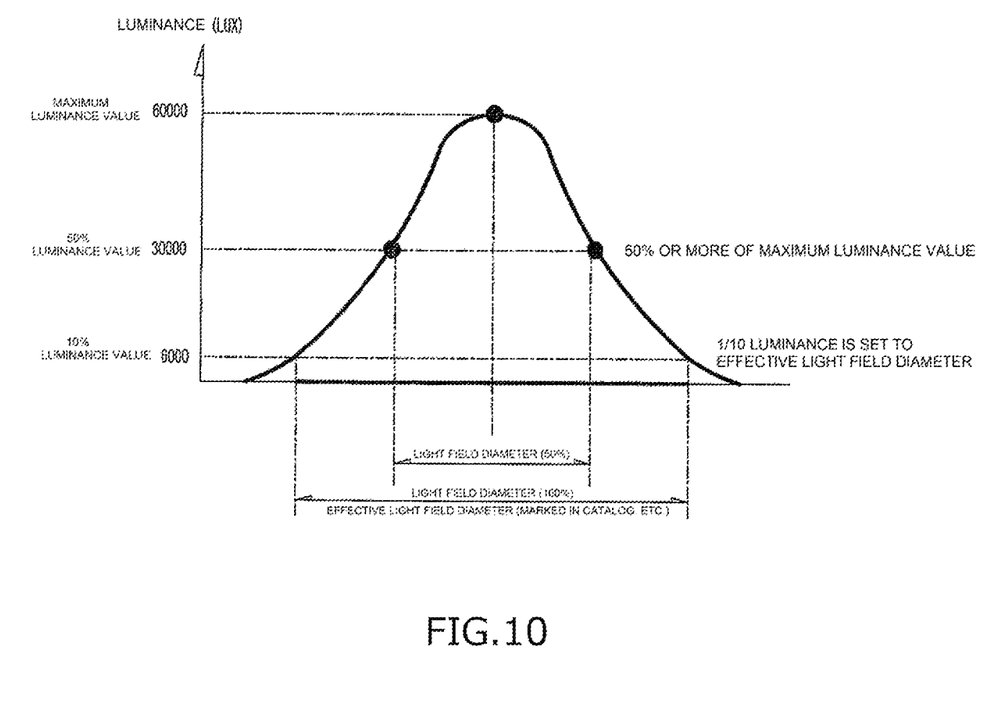
FIG. 10 is a graph illustrating an illumination condition of the IEC standard (IEC 60601-2-41).

The lens barrels 25a, 25b, and 25c are arranged such that respective optical axes X1, X2, and X3 of the condensing lenses held therein intersect one another at a position F1 in front of a position corresponding to the certain distance L (a distance from a lower end of each lens barrel to the affected part in FIG. 9). In addition, focal distances of the used condensing lenses held in the respective lens barrels are shorter than the certain distance L (a focal position by each lens is denoted by F2).

According to the configuration and the arrangement mode of the condensing lenses, irradiation light emitted from each condensing lens may overlap irradiation light from the condensing lens held by each lens barrel at the position of the certain distance L. In this way, it is possible to obtain a region of bright irradiation light (most bright 65,000 LUX at the center C of overlapping light from the three condensing lenses, and a substantially circular region R1 having 32,500 LUX or more in a range of the diameter 90 mm).

In addition, in a region outside the region R1 (a substantially annular region R2 having a diameter of 90 mm to 150 mm), a region in which irradiation diameters from the respective condensing lenses overlap each other decreases, and thus a region having darker irradiation light than that in the region R1 is obtained (a region within a range of the region R2 corresponds to the effective light field diameter). In a boundary portion therebetween (an outer peripheral edge of the region R1), illumination does not rapidly change and gradually changes (gradually blurs) with respect to the region R2, and thus an illumination gap between the affected part to be irradiated and a portion around the affected part is reduced, and visual recognition becomes easier when the medical treatment is performed.

In the above-described configuration, when the operation lever 27a is pinched and operated to slide in the left-right direction, thereby shifting the condensing lens in the axial direction, the focal position (condensing point) F2 is shifted in the optical axis direction, and thus it is possible to adjust an irradiation field (light field diameter) formed by overlapping with each other by each lens to an arbitrary size. That is, since the depth of irradiation light may be adjusted within a certain axial distance, bright irradiation light may be obtained in a pinpoint manner according to the position of the affected part (depth position of the affected part).

The helicoid mechanism described above is preferably configured such that each condensing lens is shifted in the axial direction within a range which a distance between each condensing lens and the LED light source is closer than the focal distance of each lens and a range which the distance is farther than the focal distance. That is, in a state in which the distance between each condensing lens and the LED light source is closer than the focal distance of each lens, light emitted from each lens barrel diffuses, and thus an object may be irradiated with bright illumination lights to a certain extent even though the degree of the brightness is not as high as described above. In addition, in a state in which the distance between each condensing lens and the LED light source is farther than the focal distance of each lens, light emitted from each lens barrel converges. Thus, when the operation lever 27a is operated in this state, it is possible to adjust the depth of irradiation light having high illuminance as described above.

According to such a helicoid mechanism, it is possible to switch between a state of illuminating the affected part with irradiation light at high illumination and a state of illuminating a wide range with a certain degree of illuminance, so that convenience may be improved.

In the base 21, a reflecting mirror 28 for reflecting light transmitting the condensing lens toward the affected part of the patient is installed below each lens barrel. The reflecting mirror 28 is attached to a mirror fixing shaft 30 arranged between the pair of side walls 21a at a predetermined angle and is preferably configured such that the angle may be adjusted.

Specifically, both ends of the mirror fixing shaft 30 are rotatably supported by attaching a bush 22f to a long groove 21d formed in each of the side walls 21a, and a reflection mirror rotating mechanism 32 is provided at one side thereof. The reflection mirror rotating mechanism 32 includes a nut 22g which is in surface contact with the side wall 21a to fix the mirror fixing shaft 30, and a rotation operating member (operation lever) 33 capable of operating rotation is provided in the nut 22g. The operation lever 33 protrudes toward through a long hole 3d formed at one end portion of the main body 3 (shade portion 3c). When this portion is pinched with fingers to operate rotation, it is possible to change an angle of the reflecting mirror 28 to change an irradiation range in the front-rear direction.

As described above, in case of changing the irradiation range in the present embodiment, the irradiation range may be easily changed by rotating only the lightweight reflecting mirror 28 rather than by rotating the entire light source unit 20. An arc-shaped notch 22h is formed along the circumferential direction on an outer periphery of the nut 22g. When a regulation pin 22k fixed to the side wall 21a is brought into contact with this portion, a rotation range of the reflecting mirror 28 is regulated.

The reflecting mirror 28 described above may include a cold mirror. The cold mirror transmits light having a wavelength in an infrared band, and thus it is possible to reduce radiant heat generated in the irradiation range, and to prevent the affected part from drying during the medical treatment.

Figure 6:
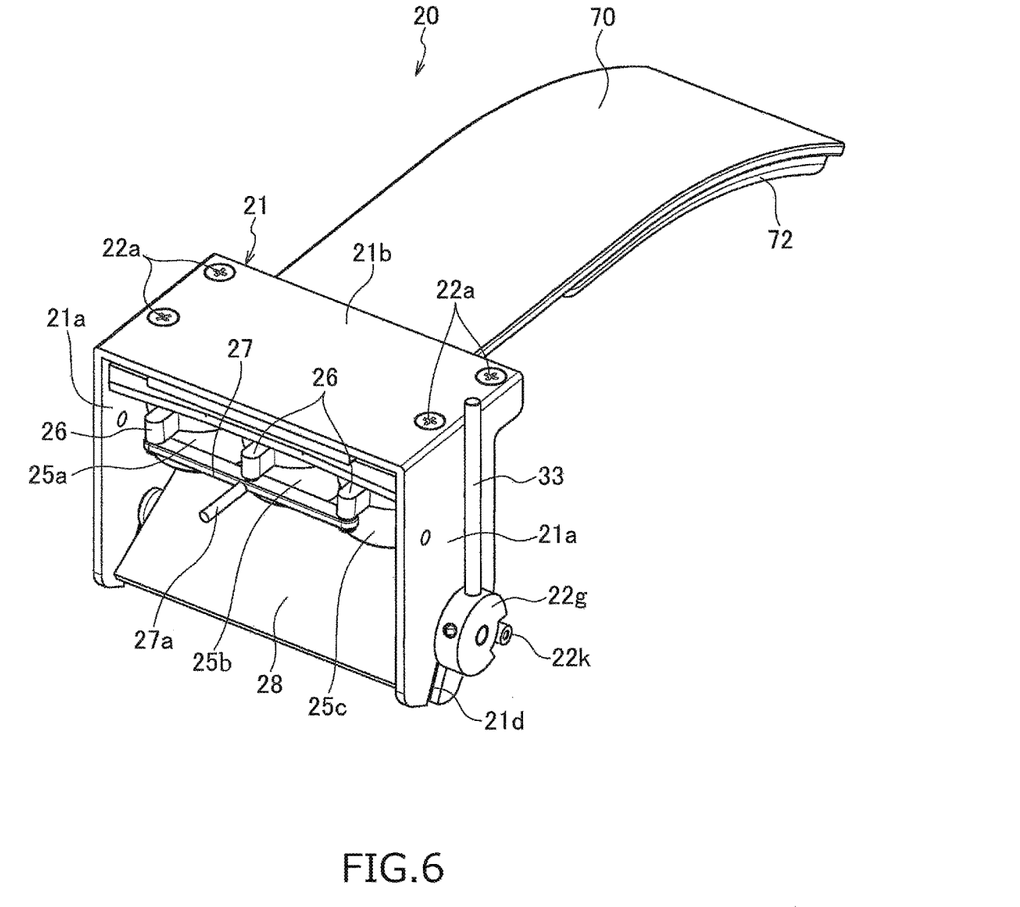
FIG. 6 is a perspective view illustrating an overall configuration of a light source unit incorporated in the lighting device.
Figure 7:
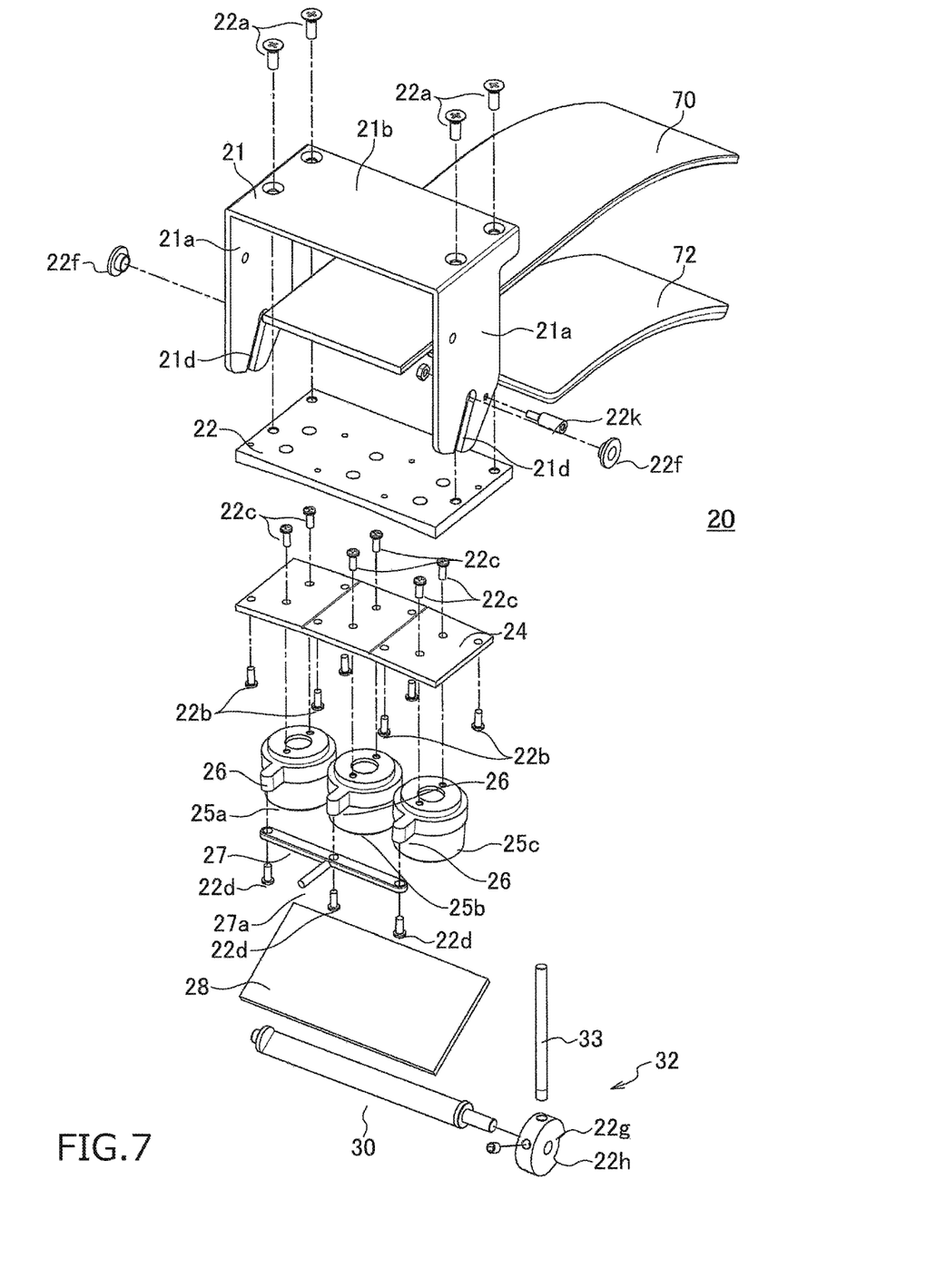
FIG. 7 is an exploded perspective view of the light source unit.
Figure 8:
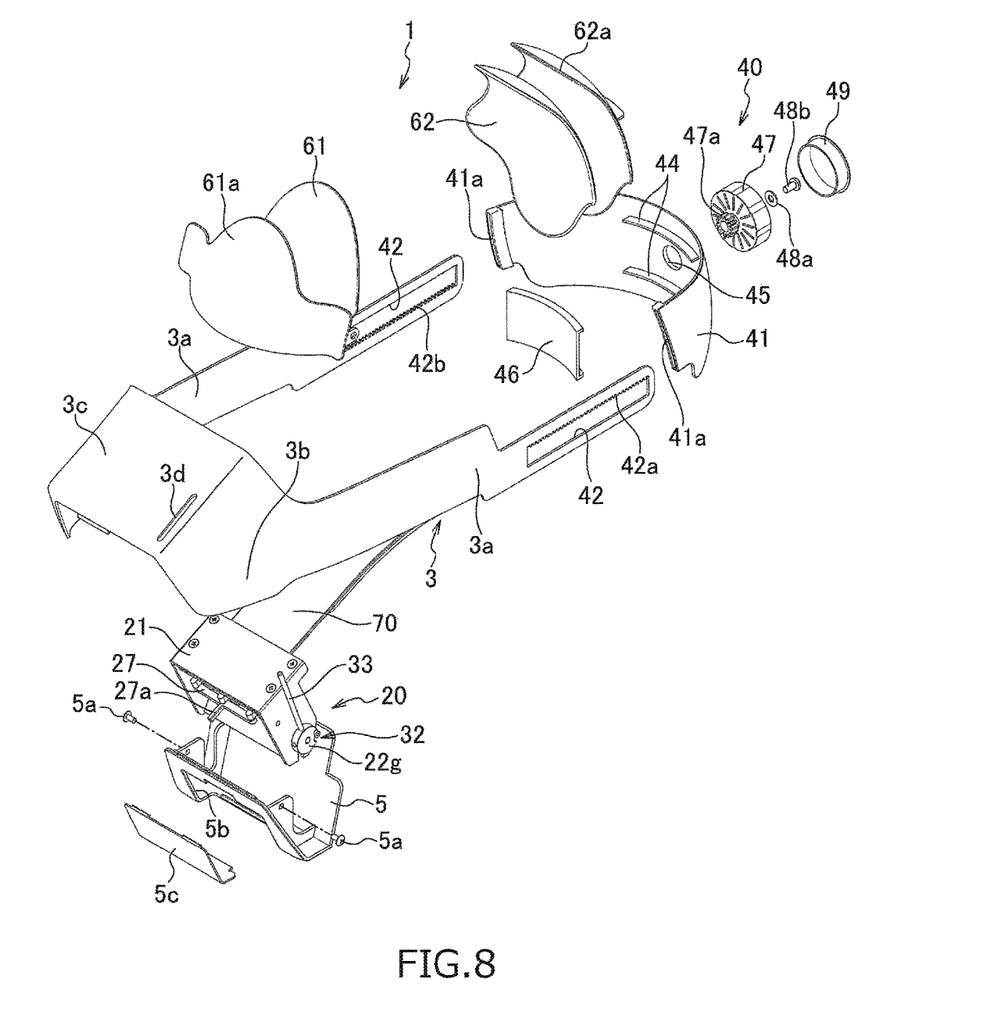
FIG. 8 is an exploded perspective view of the lighting device illustrated in FIG. 1.

The light source unit 20 integrated as illustrated in FIG. 6 is incorporated in the storage case 5. In this case, a connection terminal (not illustrated) for supplying power is provided in the light source unit 20, and there is no particular restriction on a form and an arrangement position of the connection terminal, a scheme of supplying power to the light source unit, etc. In addition, with regard to supply of power, for example, it is possible adopt a scheme of supplying power from a portable direct current (DC)-type battery, or a scheme of supplying power from a power supply (alternating current (AC) power supply) installed in a room.

Next, a description will be given of a configuration of the length adjusting mechanism 40.

The belt-shaped portion 3a attached to extend along the circumferential direction of the head H of the wearer P is configured such that the length thereof may be adjusted. In the present embodiment, the belt-shaped portion 3a is divided at the occipital region side, and a distal end region thereof has overlap. Further, the length may be adjusted by adjusting a length of the overlap. The overlap of the belt-shaped portion 3a is formed by providing a back face 41 formed to curve along a periphery of the occipital region in the main body 3, inserting the belt-shaped portion 3a into an insertion hole 41a formed at each of both sides of the back face 41, and inserting the belt-shaped portion 3a along a curved surface.

Openings 42 are formed along the longer direction in respective overlap positions of belt-shaped portions 3a, a rack 42a is formed at an upper side in an opening of one belt-shaped portion, and a rack 42b is formed at a lower side in an opening of the other belt-shaped portion. In addition, a pair of guides 44 that guides the belt-shaped portions 3a inserted from both sides and an opening 45 between the guides are formed in the back face 41, and this portion is covered by a cover (gear bearing) 46 from the inside.

The adjusting knob 47 including a pinion 47a meshing with the racks 42a and 42b formed in the openings of the belt-shaped portions is arranged in the opening 45, and the adjusting knob 47 is rotatably supported with respect to the cover 46 through a washer 48a and a stopper screw 48b. In addition, a cap 49 is attached to an operation portion of the adjusting knob 47.

According to such a length adjusting mechanism 40, when the main body 3 is put on the head H in a state in which the belt-shaped portion 3a is loosened, the front cushion member 61 and the back cushion member 62 come into contact with the head surface and are positioned. Further, when the overlap length of the overlap region of the belt-shaped portion 3a is adjusted by rotating the adjusting knob 47 in this state, fastening to the head is performed. In this way, a position at which the main body 3 is attached to the head H is stabilized.

The lighting device 1 of the present embodiment may be easily mounted only by putting the main body 3 on the head and adjusting the length of the belt-shaped portion 3a, and may irradiate the affected part of the patient with light of the same degree of brightness at a certain light field diameter even when large-scale surgical light equipment is not present. In addition, in a state in which the main body 3 is put on the head, the center of gravity is biased toward the center of the head as described above, and the weight balance is excellent when compared to a known lighting device. Thus, even when the wearer performs the medical treatment for a long time, it is possible to lighten the burden. Further, in the present embodiment, since the focal depth and the irradiation position of the light field diameter having a constant brightness may be easily changed by the operation levers 27a and 33, the operability and the handling property may be improved.

The embodiment of the invention has been described above, however, the invention is not limited to the above-described embodiment and may be variously modified. For example, the illumination or the light field diameter by the LED light source may be appropriately deformed according to a specification of the light source unit 20, for example, the number and the arrangement mode of LED elements, a refractive index of the condensing lens or the number of arranged condensing lenses, etc. In addition, the configuration or an arrangement position of the length adjusting mechanism 40 is arbitrary and may be appropriately deformed. In addition, even though the radiator plate 70 is formed in the rectangular shape, a shape thereof may be appropriately deformed. For example, a width may be widened backward such that the center of gravity position is on the rear side.

EXPLANATIONS OF LETTERS OR NUMERALS 1 lighting device
3 main body
3a belt-shaped portion
5 storage case
20 light source unit 24 LED substrate
25a, 25b, 25c lens barrel
27a, 33 operation lever
28 reflecting mirror
40 length adjusting mechanism
70 radiator plate

The invention claimed is:

1. A head-mounted type lighting device comprising:
a main body including a belt-shaped portion mounted along a circumferential direction of a head of a wearer, the main body being integrally formed using a synthetic resin;
a storage case provided in the main body and positioned in a forehead region of the wearer when the lighting device is mounted on the wearer; and
a light source unit incorporated in the storage case including a light emitting diode (LED) substrate, a plurality of LED light sources being mounted on the LED substrate, a condensing lens for condensing light emitted from the plurality of LED light sources, a reflecting mirror for deflecting light emitted from the condensing lens and reflecting the light toward an affected part of a patient, and a radiator plate extending from a forehead region toward a parietal region of the wearer for radiating heat generated from the LED substrate.

2. The head-mounted type lighting device according to claim 1, wherein a heat pipe is incorporated in the radiator plate along an extending direction.

3. The head-mounted type lighting device according to claim 1, wherein the radiator plate is formed to be curved to have a substantially uniform distance from a surface of the head of the wearer and formed to terminate at a parietal region of the wearer.

4. The head-mounted type lighting device according to claim 2, wherein the radiator plate is formed to be curved to have a substantially uniform distance from a surface of the head of the wearer and formed to terminate at a parietal region of the wearer.

5. The head-mounted type lighting device according to claim 1,
wherein the light source unit includes a reflecting mirror rotating mechanism for rotating the reflecting mirror, and
the main body is provided with a rotation operating member for manually operating the reflecting mirror rotating mechanism to rotate the reflecting mirror, thereby changing an irradiation range in a front-rear direction.

6. The head-mounted type lighting device according to claim 2,
wherein the light source unit includes a reflecting mirror rotating mechanism for rotating the reflecting mirror, and
the main body is provided with a rotation operating member for manually operating the reflecting mirror rotating mechanism to rotate the reflecting mirror, thereby changing an irradiation range in a front-rear direction.

7. The head-mounted type lighting device according to claim 3,
wherein the light source unit includes a reflecting mirror rotating mechanism for rotating the reflecting mirror, and
the main body is provided with a rotation operating member for manually operating the reflecting mirror rotating mechanism to rotate the reflecting mirror, thereby changing an irradiation range in a front-rear direction.

8. The head-mounted type lighting device according to claim 4,
wherein the light source unit includes a reflecting mirror rotating mechanism for rotating the reflecting mirror, and
the main body is provided with a rotation operating member for manually operating the reflecting mirror rotating mechanism to rotate the reflecting mirror, thereby changing an irradiation range in a front-rear direction.

9. The head-mounted type lighting device according to claim 1, wherein the reflecting mirror corresponds to a cold mirror.

10. The head-mounted type lighting device according to claim 1, wherein a shade portion protruding forward from a forehead part of the wearer is integrally formed in the main body.

11. The head-mounted type lighting device according to claim 1, wherein the main body includes a curved front cushion member and a curved back cushion member, the front cushion member contacting a head surface from an upper portion of a forehead of the wearer toward a parietal region side, the back cushion member contacting the head surface from a parietal area of the wearer toward an occipital region side when the lighting device is mounted on the wearer.

12. The head-mounted type lighting device according to claim 1,
wherein the belt-shaped portion includes an overlap portion, a rack being formed in the overlap portion along a lengthwise direction such that a length is adjustable according to a size of the head with respect to the wearer, and
a pinion member meshing with the rack is meshed with the overlap portion, and the pinion member is rotated to adjust an overlap length of the belt-shaped portion in the overlap portion, thereby adjusting the length.

* * * * *